United States Patent
Honoré et al.

(10) Patent No.: US 9,557,582 B2
(45) Date of Patent: *Jan. 31, 2017

(54) READER COMMUNICATION WITH CONTACT LENS SENSORS AND DISPLAY DEVICE

(71) Applicant: Verily Life Sciences LLC, Mountain View, CA (US)

(72) Inventors: Frank Honoré, Mountain View, CA (US); Brian Otis, Sunnyvale, CA (US); Andrew Nelson, Richmond, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,856

(22) Filed: Nov. 10, 2014

(65) Prior Publication Data

US 2015/0061837 A1  Mar. 5, 2015

Related U.S. Application Data

(63) Continuation of application No. 13/931,802, filed on Jun. 28, 2013, now Pat. No. 8,922,366.

(51) Int. Cl.
*G08B 21/00* (2006.01)
*G02C 11/00* (2006.01)
(Continued)

(52) U.S. Cl.
CPC ............... *G02C 11/10* (2013.01); *A61B 3/101* (2013.01); *A61B 5/0026* (2013.01);
(Continued)

(58) Field of Classification Search
CPC .................................................... A61B 5/0026
(Continued)

(56) References Cited

U.S. PATENT DOCUMENTS 5,791,344 A * 8/1998 Schulman .......... A61B 5/14865
204/403.11
7,809,417 B2 10/2010 Abreu
(Continued)

FOREIGN PATENT DOCUMENTS

WO 2007/015169 2/2007

OTHER PUBLICATIONS

Bluetooth SIG, "Specification of the Bluetooth System", Jun. 30, 2010, vol. 0, p. 1-vol. 2, p. 154, Core Package Version 4.0, Bluetooth SIG.

(Continued)

*Primary Examiner* — Brent Swarthout
(74) *Attorney, Agent, or Firm* — McDonnell Boehnen Hulbert & Berghoff LLP

(57) ABSTRACT

A reader for communicating with both an eye-mountable device and a display device is provided. The reader can transmit radio frequency power to a tag that is part of the eye-mountable device. The reader can communicates with the tag using a first protocol. Communicating with the tag can include having the reader request data from the tag and receive the requested data from the tag. The reader can process the received data. The reader can store the processed data. The reader can communicates with the display device using a second protocol, where the first and second protocols can differ. Communicating with the display device can include having the reader transmit the stored data to the display device. The display device can receive the transmitted data, process the transmitted data, and generate one or more displays including the transmitted and/or processed data.

20 Claims, 10 Drawing Sheets

(51) Int. Cl.
A61B 5/00 (2006.01)
A61B 5/145 (2006.01)
G06K 7/10 (2006.01)
A61B 3/10 (2006.01)
A61B 5/1477 (2006.01)
G02C 7/04 (2006.01)

(52) U.S. Cl.
CPC ........ *A61B 5/1477* (2013.01); *A61B 5/14532* (2013.01); *A61B 5/6821* (2013.01); *G02C 7/04* (2013.01); *G06K 7/10158* (2013.01); *G06K 7/10386* (2013.01); *A61B 5/7445* (2013.01); *A61B 2560/0219* (2013.01); *A61B 2560/0223* (2013.01); *G02C 7/049* (2013.01)

(58) Field of Classification Search
USPC ............ 340/572.1, 539.12, 5.82, 10.1, 539.1,340/870.16; 345/8; 351/158, 159.4
See application file for complete search history.

(56) References Cited

U.S. PATENT DOCUMENTS

| | | | |
|---|---|---|---|
| 8,096,654 B2* | 1/2012 | Amirparviz et al. | 351/159.4 |
| 8,922,366 B1* | 12/2014 | Honore et al. | 340/539.12 |
| 2003/0211625 A1* | 11/2003 | Cohan et al. | 436/95 |
| 2005/0114154 A1* | 5/2005 | Wolkowicz et al. | 705/1 |
| 2006/0232426 A1 | 10/2006 | Sabeta | |
| 2006/0267731 A1 | 11/2006 | Chen | |
| 2009/0128448 A1 | 5/2009 | Riechel | |
| 2009/0143761 A1* | 6/2009 | Cantor | A61N 1/044 604/501 |
| 2009/0243969 A1* | 10/2009 | Matsubara et al. | 345/8 |
| 2010/0103368 A1 | 4/2010 | Amirparviz et al. | |
| 2010/0253479 A1* | 10/2010 | Cunningham et al. | 340/10.1 |
| 2011/0163850 A1 | 7/2011 | Bachman et al. | |
| 2012/0245444 A1 | 9/2012 | Otis et al. | |
| 2012/0259188 A1 | 10/2012 | Besling | |
| 2013/0024384 A1 | 1/2013 | Beenau et al. | |
| 2013/0090062 A1 | 4/2013 | Tricoukes et al. | |
| 2013/0127635 A1 | 5/2013 | Goodnow et al. | |
| 2014/0275923 A1* | 9/2014 | Haffner et al. | 600/377 |

OTHER PUBLICATIONS

Bluetooth SIG, "Specification of the Bluetooth System", Jun. 30, 2010, vol. 2, pp. 155-554, Core Package Version 4.0, Bluetooth SIG.
Bluetooth SIG, "Specification of the Bluetooth System", Jun. 30, 2010, vol. 2, pp. 555-954, Core Package Version 4.0, Bluetooth SIG.
Bluetooth SIG, "Specification of the Bluetooth System", Jun. 30, 2010, vol. 2, p. 955—vol. 3, p. 240, Core Package Version 4.0, Bluetooth SIG.
Bluetooth SIG, "Specification of the Bluetooth System", Jun. 30, 2010, vol. 3, pp. 241-440, Core Package Version 4.0, Bluetooth SIG.
Bluetooth SIG, "Specification of the Bluetooth System", Jun. 30, 2010, vol. 3, p. 441—vol. 6, p. 138, Core Package Version 4.0, Bluetooth SIG.
D. Diamond et al., "Wireless Sensor Networks and Chemo-Biosensing", Chemical Reviews, Jan. 24, 2008, pp. 652-679, vol. 108, No. 2, American Chemical Society.
EPCGlobal Inc.,"EPCTM Radio—Frequency Identity Protocols Class-1 Generation-2 UHF RFID Protocol for Communications at 860 MHz-960 MHz, Version 1.2.0", Oct. 23, 2008, EPC Global Inc.
Healthwise Staff, "Diabetes Health Center Blood Glucose", WebMD, Jul. 5, 2011, Healthwise, Inc.
Wikimedia Foundation, "Blood Sugar", May 10, 2013, Wikimedia Foundation, Inc.
International Searching Authority, International Search Report and Written Opinion, International Application No. PCT/US2014/042526, mailed Oct. 7, 2014.

* cited by examiner

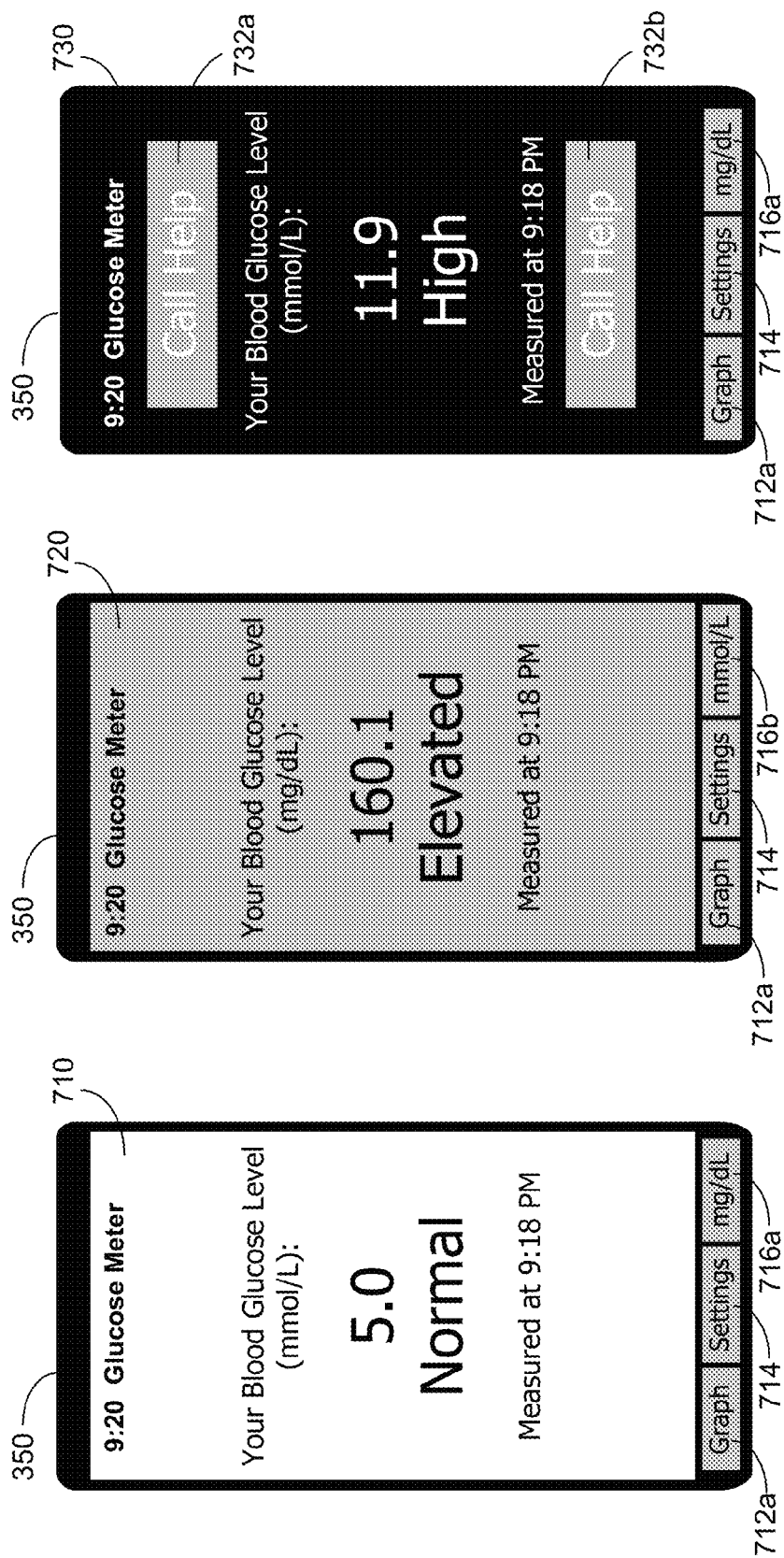

READER COMMUNICATION WITH CONTACT LENS SENSORS AND DISPLAY DEVICE

CROSS REFERENCE TO RELATED APPLICATIONS

The present application is a continuation of U.S. patent application Ser. No. 13/931,802, filed Jun. 28, 2013, now U.S. Pat. No. 8,922,366, which is hereby incorporated by reference into the present application.

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode. A counter electrode and/or reference electrode is used to complete a circuit with the working electrode and allow the generated current to flow. When the working electrode is appropriately biased, the output current can be proportional to the reaction rate, so as to provide a measure of the concentration of the analyte surrounding the working electrode.

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

One aspect of the present disclosure provides a method. A reader transmits radio frequency power to a tag. The tag is part of an eye-mountable device. The reader communicates with the tag using a first protocol. Communicating with the tag includes: requesting data from the tag and receiving the requested data from the tag. The reader processes the received data. The reader stores the processed data. The reader communicates with a display device using a second protocol. Communicating with the display device includes transmitting the stored data to the display device. The first protocol differs from the second protocol.

Another aspect of the present disclosure provides a non-transitory computer-readable storage medium. The non-transitory computer-readable storage medium has stored thereon program instructions that, upon execution by a processor of a computing device, cause the computing device to perform functions. The functions include: transmitting radio frequency (RF) power to a tag, where the tag is part of an eye-mountable device, communicating with the tag using a first protocol, where communicating with the tag includes requesting data from the tag and receiving the requested data from the tag; processing the received data from the tag; storing the processed data; and communicating with a display device using a second protocol, where communicating with the display device includes transmitting the stored data to the display device, and where the first protocol differs from the second protocol.

Yet another aspect of the present disclosure provides a computing device. The computing device includes an antenna, a processor, and a non-transitory computer readable medium. The non-transitory computer readable medium stores instructions thereon that, when executed by the processors, cause the computing device to perform functions. The functions include: transmitting radio frequency (RF) power to a tag using the antenna, where the tag is part of an eye-mountable device, communicating with the tag using a first protocol, where communicating with the tag includes requesting data from the tag and receiving the requested data from the tag; processing the received data from the tag; storing the processed data; and communicating with a display device using a second protocol, where communicating with the display device includes transmitting the stored data to the display device, and where the first protocol differs from the second protocol.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIGS. 7A-7E show example views of a user interface for a display device, in accordance with an example embodiment.

DETAILED DESCRIPTION

I. Overview

Figure 1:
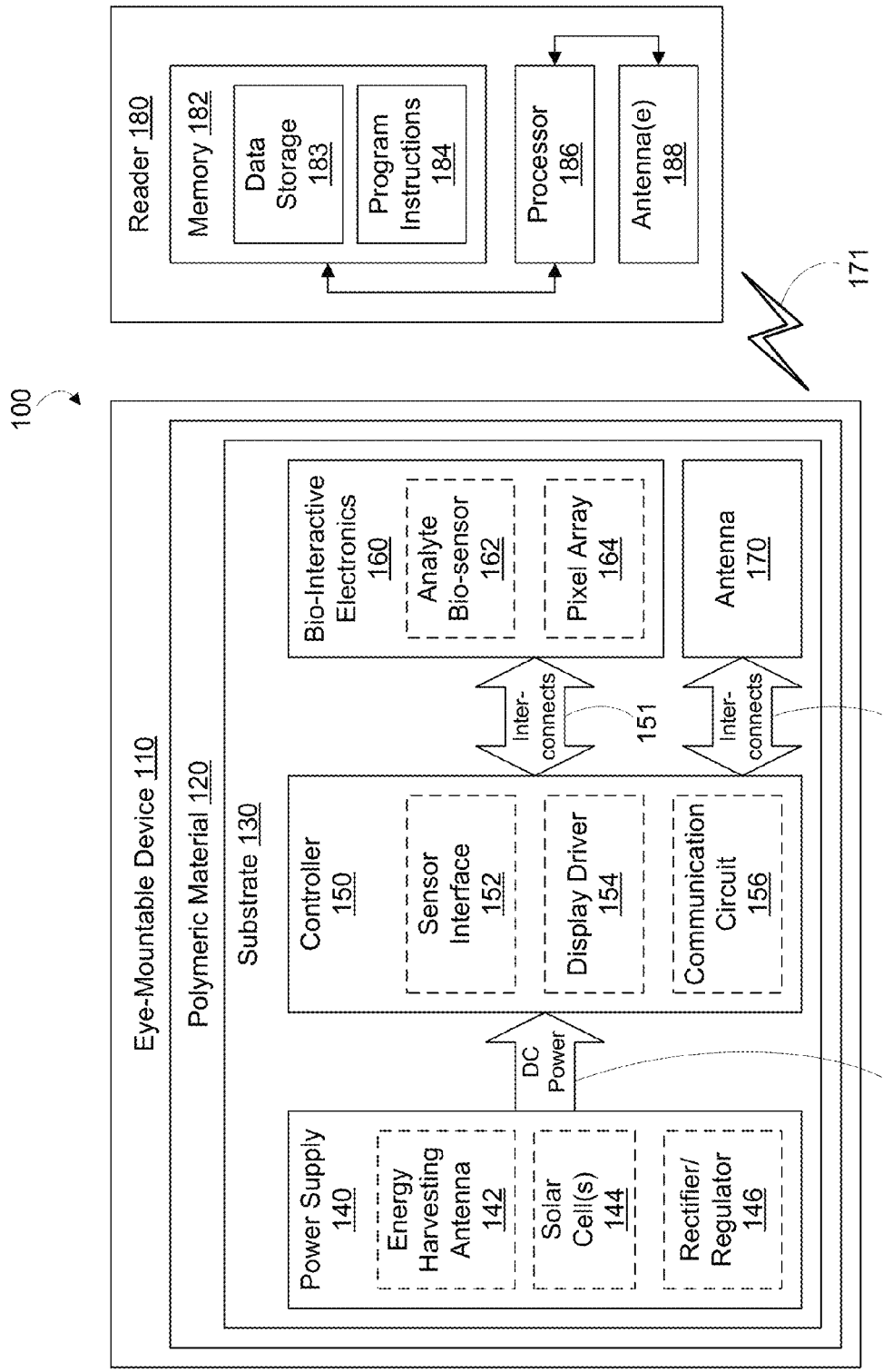
FIG. 1 is a block diagram of an example system that includes an eye-mountable device in wireless communication with a reader, in accordance with an example embodiment.

An ophthalmic sensing platform or implantable sensing platform can include a sensor, control electronics and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to a reader via the antenna.

In some examples, the polymeric material can be in the form of a round lens with a concave curvature configured to mount to a corneal surface of an eye, such as a contact lens. The substrate can be embedded near the periphery of the polymeric material to avoid interference with incident light received closer to the central region of the cornea. The sensor can be arranged on the substrate to face inward, toward the corneal surface, so as to generate clinically relevant readings from near the surface of the cornea and/or from tear fluid interposed between the polymeric material and the corneal surface. Additionally or alternatively, the sensor can be arranged on the substrate to face outward, away from the corneal surface and toward the layer of tear fluid coating the surface of the polymeric material exposed to the atmosphere. In some examples, the sensor is entirely embedded within the polymeric material. For example, an electrochemical sensor that includes a working electrode and a reference electrode can be embedded in the polymeric material and situated such that the sensor electrodes are less than 10 micrometers from the polymeric surface configured to mount to the cornea. The sensor can generate an output signal indicative of a concentration of an analyte that diffuses through the lens material to the sensor electrodes.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. An ophthalmic sensing platform including the above-mentioned sensor can be configured to measure one or more of these analytes can thus provide a convenient non-invasive platform useful in diagnosing and/or monitoring health states. For example, an ophthalmic sensing platform can be configured to sense glucose and can be used by diabetic individuals to measure/monitor their glucose levels. In some embodiments, the sensor can be configured to measure additional or other conditions other than analyte levels; e.g., the sensor can be configured to such as light, temperature, and current measurements, An external reader device or "reader" can radiate radio frequency radiation to power the sensor. The reader may thereby control the operation of the sensing platform by controlling the supply of power to the sensing platform. In some examples, the reader can operate to intermittently interrogate the sensing platform to provide a reading by radiating sufficient radiation to power the sensing platform to obtain a measurement and communicate the result. The reader can also store the sensor results communicated by the sensing platform. In this way, the reader can acquire a series of analyte concentration measurements over time without continuously powering the sensing platform.

The sensor of the ophthalmic sensing platform can be configured with, or be part of, a Radio-frequency Identification (RFID) tag. The RFID tag and reader can communicate using an RFID protocol; e.g., an RFID Generation 2 protocol. The RFID tag can be configured to receive radio signals from the reader. In some embodiments, the reader's signals can be used for both communicating with and powering the RFID tag; while in other embodiments, the RFID tag can be a powered device; e.g., be configured with a battery that powers the tag.

The reader can communicate with other devices than the RFID tag. As one possible example, the reader can be equipped with a Bluetooth interface as well as with an RFID interface. The reader can communicate with other devices, e.g., a display device, via a Bluetooth or other protocol. In one example, the reader can obtain data from the RFID tag using RFID command(s); e.g., the RFID Generation 2 standard Read command. Upon obtaining the data, the reader can store, process, and/or communicate the data using the Bluetooth interface to another device, such as the display device. Other interfaces for communicating with devices using other communication protocol(s) are possible as well.

As an example, the above-mentioned contact lens can be configured with a sensor that includes an RFID tag. As mentioned above, the sensor can be configured to take measurements while being worn in an eye of a wearer. Upon taking the measurements, the sensor may store data related to the measurements, and subsequently send the data upon request from the reader. The reader, in turn, can store and/or process the received data. For example, the sensor can take current measurements of an analyte (e.g., glucose) in tear film of the eye of the wearer and send data about the measured current(s) to the reader. The reader can process the current measurement data to determine analyte-related information about the wearer.

The tear-film analyte concentration information can be sent from the reader to a display device. The display device could be, for example, a wearable, laptop, desktop, handheld, or tablet computer, a mobile phone, or a subsystem of such a device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data.

In some embodiments, the reader and the display device can be configured with configuration data to perform glucose-related processing. For example, the reader can include configuration data such as current measurement data for various levels of glucose concentration. Based on this configuration data, the reader can determine a tear-film glucose concentration for the wearer. Also, the wearer can provide blood glucose concentration(s) and corresponding tear-film glucose concentration(s) for the wearer to the display device (for example, during configuration), and the display device can determine relationships between blood glucose concentration(s) and tear-film glucose concentration(s).

During operation of these embodiments, the RFID tag in an eye of the wearer can generate tear-film current data and send the tear-film current data to the reader. The reader can then process the tear-film current data to generate tear-film glucose concentration(s) and send the tear-film glucose concentration(s) to the display device. Then, the display device can be configured to receive tear-film glucose concentration(s) from the reader and generate corresponding blood glucose concentration(s). In particular embodiments, either the reader or the display device can take tear-film current data as inputs and generate blood glucose concentration(s) as output(s); i.e., all processing can take place at either the reader or display device.

In some embodiments, the reader can be configured to be frequently worn in proximity to one or more contact lenses configured with sensors worn by a person. For example, the reader can be configured to be part of a pair of eyeglasses, jewelry (e.g., earrings, necklace), headband, head cover such as a hat or cap, earpiece, other clothing (e.g., a scarf), and/or other devices. As such, the reader can provide power and/or receive measurements while proximate to the worn contact lens(es).

Configuring the reader to be frequently worn in proximity to one or more contact lenses enables the lenses to have a reliable external power source and/or storage for sensor data collection, processing of sensor data, and transmission of unprocessed and/or processed sensor data to additional devices; e.g., the above-mentioned display device. Thus, the herein-described reader can provide valuable support functionality, including but not limited to power, communication, and processing resources, to enhance use of contact lenses with embedded sensors, while enabling consequent reduction of support functions on the contact lens. This reduction of support functions on the contact lens may free resources on the contact lens to enable addition of more and/or different sensors and to provide for other functionality on the contact lens.

II. Example Ophthalmic Electronics Platform

FIG. 1 is a block diagram of a system 100 that includes an eye-mountable device 110 in wireless communication with a reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

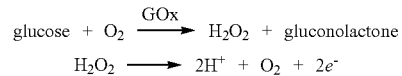

$$\text{glucose} + O_2 \xrightarrow{\text{GOx}} H_2O_2 + \text{gluconolactone}$$
$$H_2O_2 \longrightarrow 2H^+ + O_2 + 2e^-$$

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The reader 180 can be configured to be external to the eye; i.e., is not part of the eye-mountable device. Reader 180 can include one or more antennae 188 to send and receive wireless signals 171 to and from the eye-mountable device 110. In some embodiments, reader 180 can communicate using hardware and/or software operating according to one or more standards, such as, but not limited to, a RFID standard, a Bluetooth standard, a Wi-Fi standard, a Zigbee standard, etc.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that allows for retrieving information communicated from the eye-mountable device 110 (e.g., sensor outputs from the analyte bio-sensor 162). The reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

In some embodiments, reader 180 can be a smart phone, digital assistant, or other portable computing device with wireless connectivity sufficient to provide the wireless communication link 171. In other embodiments, reader 180 can be implemented as an antenna module that can be plugged in to a portable computing device; e.g., in scenarios where the communication link 171 operates at carrier frequencies not commonly employed in portable computing devices. In even other embodiments discussed below in more detail in the context of at least FIG. 5, the reader 180 can be a special-purpose device configured to be worn relatively near a wearer's eye to allow the wireless communication link 171 to operate with a low power budget. For example, the reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the reader 180 (e.g., via the communication circuit 156). The sensor reading can be communicated by, for example, modulating an impedance of the communication antenna 170 such that the modulation in impedance is detected by the reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the reader 180 can accumulate a set of analyte concentration measurements over time without continuously powering the eye-mountable device 110.

Figure 2A:
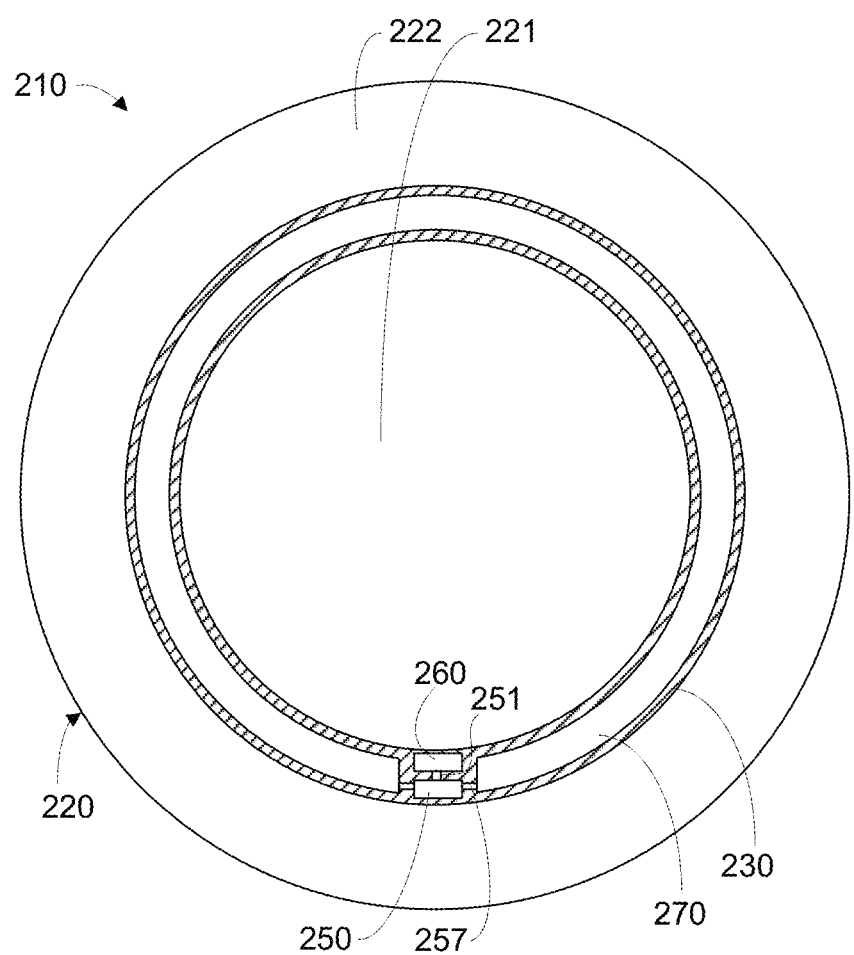
FIG. 2A is a bottom view of an example eye-mountable device, in accordance with an example embodiment.
Figure 2B:
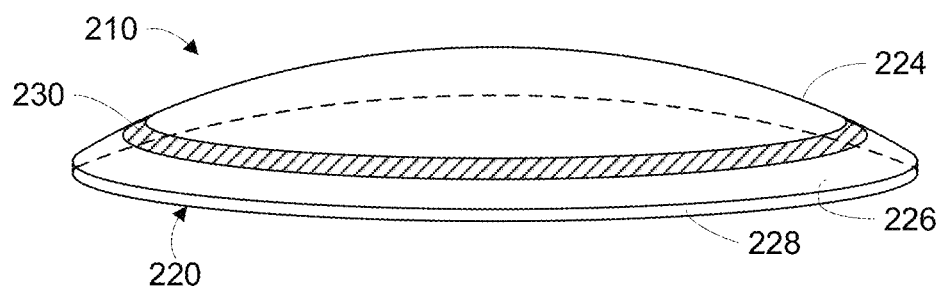
FIG. 2B is a side view of the example eye-mountable device shown in FIG. 2A, in accordance with an example embodiment.

FIG. 2A is a bottom view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. In some embodiments, eye-mountable device 210 can include some or all of the above-mentioned aspects of eye-mountable device 110. In other embodiments, eye-mountable device 110 can further include some or all of the herein-mentioned aspects of eye-mountable device 210.

The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the eye-mountable device 210, bio-interactive electronics 260 is mounted to a side of the substrate 230 facing the convex surface 224. Where the bio-interactive electronics 260 includes an analyte bio-sensor, for example, mounting such a bio-sensor on the substrate 230 facing the convex surface 224 allows the bio-sensor to sense analyte concentrations in tear film through channel 272 (shown in FIGS. 2C and 2D) in the polymeric material 220 to convex surface 224. In some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the loop antenna can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
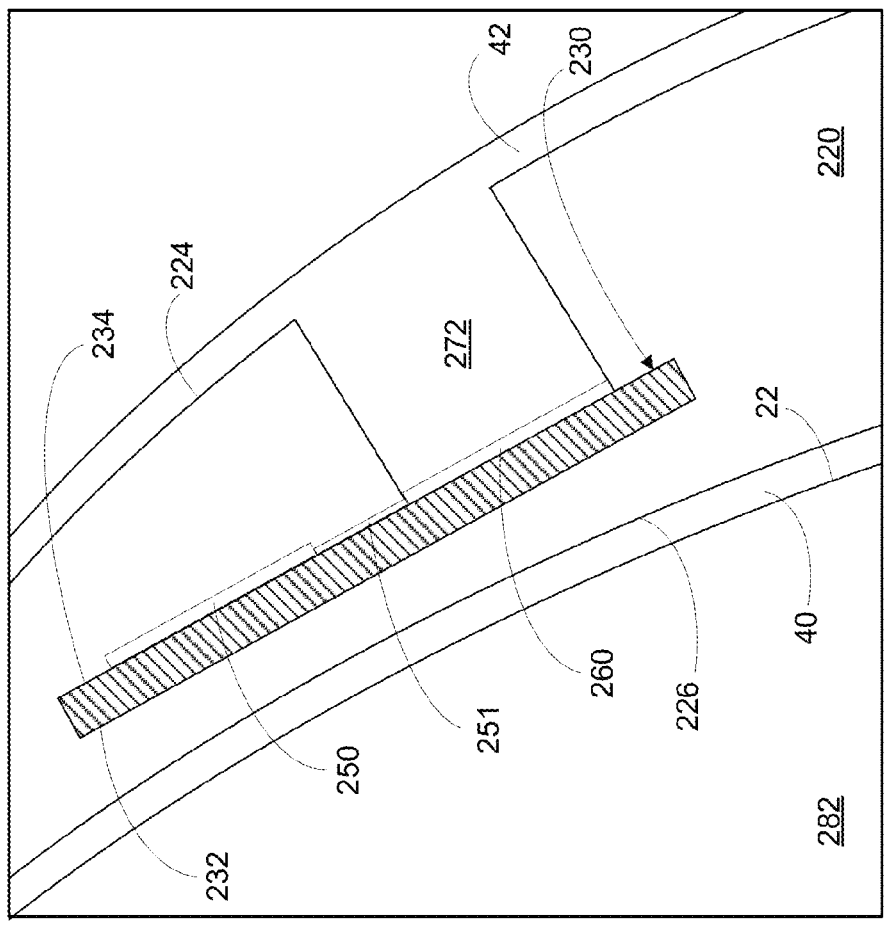
FIG. 2D is a side cross-section view enhanced to show the tear film layers surrounding the surfaces of the example eye-mountable device when mounted as shown in FIG. 2C, in accordance with an example embodiment.
Figure 2C:
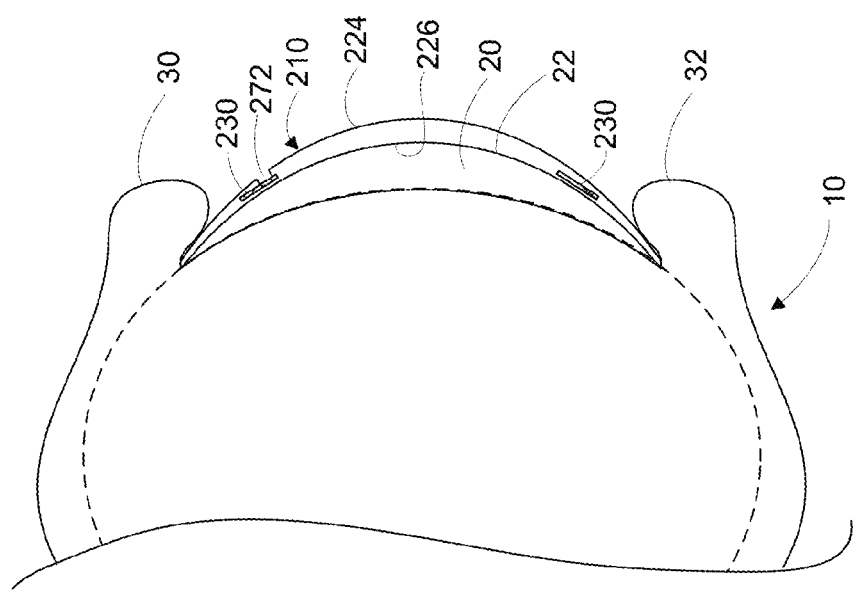
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the drawings. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (facing concave surface 226 of the polymeric material 220) and an outward-facing surface 234 (facing convex surface 224). The substrate 230 can have electronic components and/or patterned conductive materials mounted to either or both mounting surfaces 232, 234. As shown in FIG. 2D, the bio-interactive electronics 260, controller 250, and conductive interconnect 251 are mounted on the outward-facing surface 234 such that the bio-interactive electronics 260 are facing convex surface 224.

The polymer layer defining the anterior side may be greater than 50 micrometers thick, whereas the polymer layer defining the posterior side may be less than 150 micrometers. Thus, bio-interactive electronics 260 may be at least 50 micrometers away from the convex surface 224 and may be a greater distance away from the concave surface 226. However, in other examples, the bio-interactive electronics 260 may be mounted on the inward-facing surface 232 of the substrate 230 such that the bio-interactive electronics 260 are facing concave surface 226. The bio-interactive electronics 260 could also be positioned closer to the concave surface 226 than the convex surface 224. With this arrangement, the bio-interactive electronics 160 can receive analyte concentrations in the tear film 292 through the channel 272.

III. An Ophthalmic Electrochemical Analyte Sensor

Figure 3:
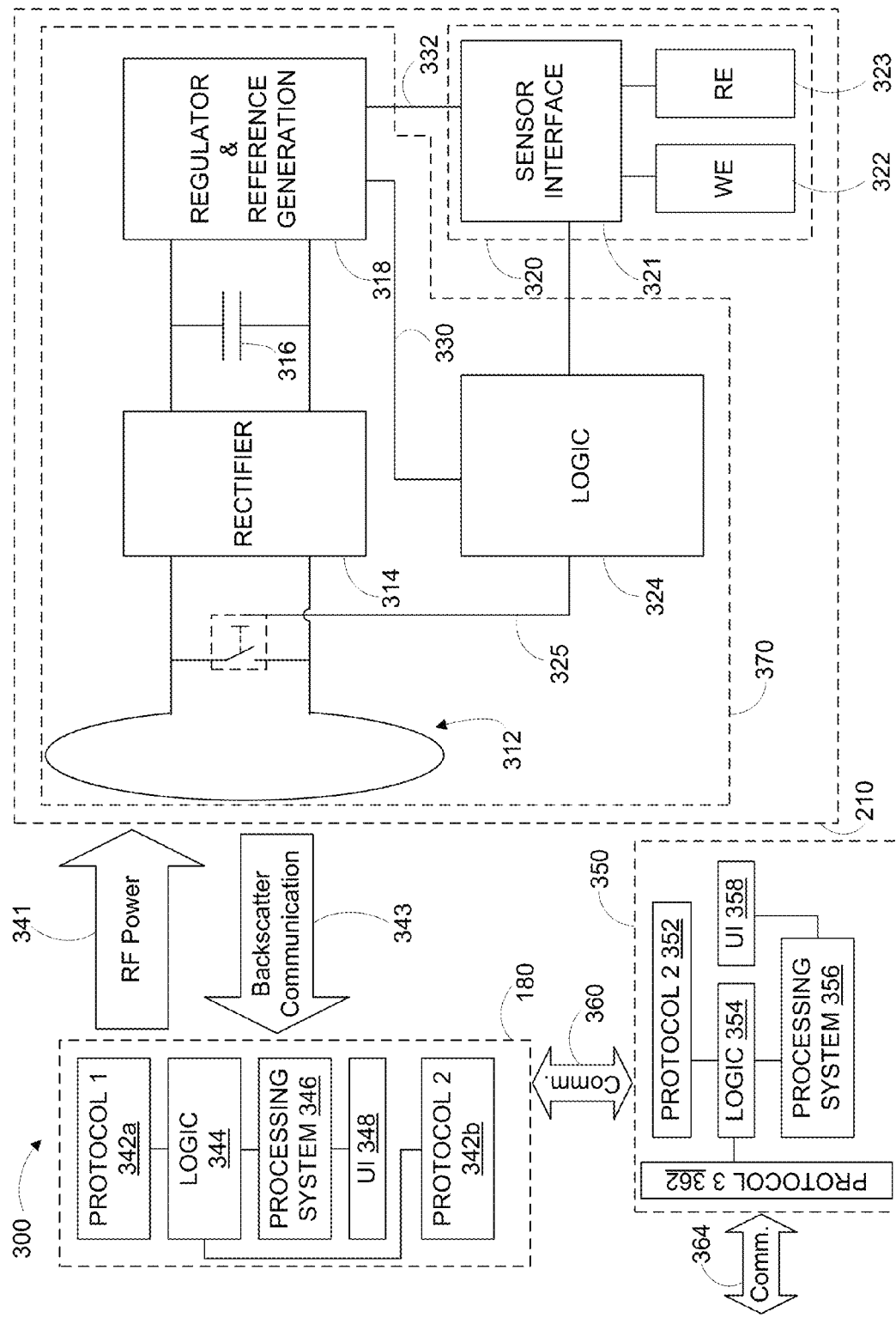
FIG. 3 is a functional block diagram of an example system for electrochemically measuring a tear film analyte concentration, in accordance with an example embodiment.

FIG. 3 is a functional block diagram of a system 300 for electrochemically measuring and displaying a tear film analyte concentration. The system 300 includes an eye-mountable device 210 with embedded electronic components in communication with and powered by reader 180. Reader 180 can also be configured to communicate with display device 350. Reader 180 and eye-mountable device 210 can communicate according to one communication protocol or standard, shown in FIG. 3 as Protocol 1, and reader 180 and display device 350 can communicate according to one communication protocol or standard, shown in FIG. 3 as Protocol 2. In some embodiments, Protocol 1 and Protocol 2 are the same; while in other embodiments, Protocol 1 differs from Protocol 2. In particular embodiments, Protocol 1 is an RFID protocol and Protocol 2 is either a Bluetooth protocol, Wi-Fi protocol, or ZigBee protocol. In other particular embodiments, Protocol 1 is either a Bluetooth protocol, a Wi-Fi protocol, or a ZigBee protocol. In still other particular embodiments, Protocol 2 is a wired protocol; such as, but not limited to, a Universal Serial Bus protocol, a Registered Jack protocol (e.g., RJ-25), or a wired Local Area Network protocol (e.g., Ethernet).

The eye-mountable device 210 includes an antenna 312 for capturing radio frequency (RF) power 341 from the reader 180. In some embodiments, RF power 341 and/or backscatter communication 343 can be provided in accordance with a communications standard or protocol, such as Protocol 1 shown in FIG. 3.

The eye-mountable device 210 includes rectifier 314, energy storage 316, and regulator 318 for generating power supply voltages 330, 332 to operate the embedded electronics. The eye-mountable device 210 includes an electrochemical sensor 320 with a working electrode 322 and a reference electrode 323 driven by a sensor interface 321. The eye-mountable device 210 includes hardware logic 324 for communicating results from the sensor 320 to the reader 180 by modulating the impedance of the antenna 312. An impedance modulator 325 (shown symbolically as a switch in FIG. 3) can be used to modulate the antenna impedance according to instructions from the hardware logic 324. Similar to the eye-mountable device 110 discussed above in connection with FIG. 1, the eye-mountable device 210 can include a mounting substrate embedded within a polymeric material configured to be mounted to an eye.

The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 210 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 210 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

In other embodiments, sensor 320 can further include and/or be replaced by sensor(s) that measure light, heat/temperature, blood pressure, air flow, and/or other characteristics than analyte concentration(s). In these other embodiments, sensor 320 can communicate data about the measured characteristics to reader 180 using backscatter communication 343 as discussed below.

The rectifier 314, energy storage 316, and voltage regulator 318 operate to harvest energy from received RF power 341. RF power 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the RF power 341 from the reader 180 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the reader 180 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance are detected by the reader 180 via the backscatter signal 343.

Reader 180 can include Protocol 1 front end 342a and logic components 344 to communicate using Protocol 1, decode the information indicated by the backscatter signal 343, provide digital inputs to a processing system 346 and receive inputs and/or provide outputs via user interface 348. Protocol 1 can be, for example, an RFID protocol. In some embodiments, part or all of eye-mountable device 210 can be configured to perform some or all features of an RFID tag. For example, as shown in FIG. 3, some or all of the components shown as tag 370 of eye-mountable device 210 can perform some or all features of an RFID tag; e.g., antenna 312, rectifier 314, energy storage 316, voltage regulator 318, hardware logic 324, etc.

In some embodiments, one or more of the features shown as separate functional blocks can be implemented ("packaged") on a single chip. For example, the eye-mountable device 210 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

A processing system, such as, but not limited to, processing system 346 or processing system 356, can include one or more processors and one or more storage components. Example processor(s) include, but are not limited to, CPUs, Graphics Processing Units (GPUs), digital signal processors (DSPs), application specific integrated circuits (ASICs). Example storage component(s) include, but are not limited to volatile and/or non-volatile storage components, e.g., optical, magnetic, organic or other memory, disc storage; Random Access Memory (RAM), Read-Only Memory (ROM), flash memory, optical memory unit, and disc memory. The storage component(s) can be configured to store software and data; e.g., computer-readable instructions configured, when executed by a processor of the processing system, to cause the processing system to carry out functions such as but not limited to the herein-described functions of reader 180, eye-mountable device 210, and/or display device 350.

The reader 180 can associate the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory either on display device 350 or through a network).

User interface 348 of reader 180 can include an indicator, such as but not limited to one or more light-emitting diodes (LEDs), that can indicate that reader 180 is operating and provide some information about its status. For example, reader 180 can be configured with an LED that displays one color (e.g., green) when operating normally and another color (e.g., red) when operating abnormally. In other embodiments, the LED(s) can change display when processing and/or communicating data in comparison to when idle (e.g., periodically turn on and off while processing data, constantly stay on or constantly stay off while idle).

In some embodiments, one or more of the LED(s) of user interface 348 can indicate a status of sensor data; e.g., not display when sensor data are either within normal range(s) or unavailable, display in a first color when sensor data are either outside normal range(s) but not extremely high or low, and display a second color when the sensor data are extremely high and/or low. For example, if sensor data indicate that blood-glucose levels are extremely high or low, user interface 348 can be instructed by processing system 346 to display using the second color. In particular embodiments, user interface 348 can include a speaker or other sound-emitting device to permit reader 180 to generate sounds; e.g., warning sound(s) and/or tone(s) if sensor data are extremely high and/or low.

In even other embodiments, reader 180 can have one or more buttons and/or other devices to receive inputs. For example, reader 180 can have a calibration button to indicate when calibration data is to be generated, such as discussed below in more detail in the context of at least FIG. 6.

In some embodiments, reader 180 can communicate with devices in addition to eye-mountable device 210/tag 370. For example, FIG. 3 shows communication 360 between reader 180 and display device 350 using Protocol 2.

To communicate with display device 350, reader 180 can include Protocol 2 front end 342b and hardware logic 344 can be configured to use Protocol 2 front end 342b to communicate using Protocol 2. In some embodiments, processing system 346 can be configured to include and/or perform the herein-described functionality of hardware logic 344.

FIG. 3 shows that display device 350 can include Protocol 2 front end 352, hardware logic 354, processing system 356, and user interface (UI) 358. Hardware logic 354 can be configured to use Protocol 2 front end 352 to communicate using Protocol 2 with at least reader 180. Processing system 356 can include computer-readable instructions that, when executed, are configured to perform some or all the herein-described functions of display system 350. In some embodiments, processing system 356 can be configured to include and/or perform the herein-described functionality of hardware logic 354. UI 358 can be configured with hardware and/or software configured to present images, text, sound, haptic feedback, etc., such as, but not including, presenting images, text, audio, and/or video information related to data received from reader 180 as part of communication 360. See FIGS. 7A-7E below for example views that can be provided by display device 350.

In some embodiments, display device 350 can include Protocol 3 front end 362. In these embodiments, hardware logic 354 can be configured to use Protocol 3 front end 362 to for sending and receiving communications 364 using Protocol 3 with one or more other devices (not shown in FIG. 3). Protocol 3 can include one or more wireless protocols, such as, but not limited to, a RFID protocol, a Bluetooth protocol, a Wi-Fi protocol, a ZigBee protocol, a WiMax protocol, or a Wireless Wide Area Network protocol (e.g., TDMA, CDMA, GSM, UMTS, EV-DO, LTE) and/or one or more wired protocols; such as, but not limited to, a Universal Serial Bus protocol, a Registered Jack protocol (e.g., RJ-25), or a wired Local Area Network protocol (e.g., Ethernet). In particular of these embodiments, Protocol 2 front end 352 and Protocol 3 front end 362 can be combined.

In embodiments utilizing Protocol 3, display device 350 can be used to forward and/or bridge data with the one or more other devices. In particular of these embodiments, a device of the one or more other devices can be a server configured to run one or more applications for collecting data from display device 350; e.g., a cloud data collection application.

IV. Example Electrochemical Sensor

Figure 4A:
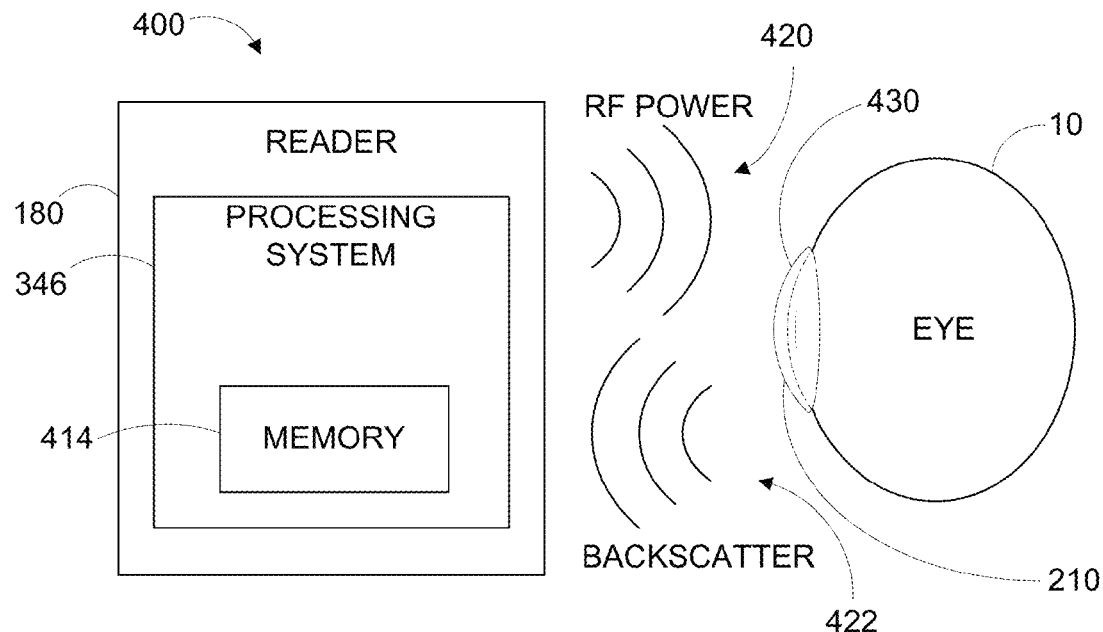
FIG. 4A is a block diagram of an ophthalmic electrochemical sensor system operated by a reader to obtain a series of amperometric current measurements over time, in accordance with an example embodiment.

FIG. 4A is a block diagram of a system 400 with eye-mountable device 210 operated by a reader 180 to obtain a series of amperometric current measurements over time. An ophthalmic electrochemical sensor; e.g., an embodiment of sensor 320, can be included with eye-mountable device 210. As shown in FIG. 4A, eye-mountable device 210 is configured to be contact-mounted over a corneal surface of an eye 10. The ophthalmic electrochemical sensor can be operated to be transitioned into an active measurement mode in response to receiving a measurement signal from the reader 180.

The reader 180 includes a processing system 346, configured with memory 414. The processing system 412 can be a computing system that executes computer-readable instruction stored in the memory 414 to cause the reader 180/system 400 to obtain a time series of measurements by intermittently transmitting a measurement signal to eye-mountable device 210. In response to the measurement signal, one or more sensors of eye-mountable device 210; e.g., ophthalmic electrochemical sensor 430, can take measurement(s), obtain results of the measurement(s), and communicate the results as shown in connection to reader 180 via backscatter 422. As discussed above regarding FIG. 3, reader 180 can provide RF power, such as RF power 420, to be harvested by the eye-mountable device 210. For example, impedance of an antenna of eye-mountable device 210 can be modulated in accordance with the sensor result such that the backscatter radiation 422 indicates the sensor results. Reader 180 can also use memory 414 to store indications of amperometric current measurements communicated by the ophthalmic electrochemical sensor 430. The reader 180 can thus be operated to intermittently power the ophthalmic electrochemical sensor 430 so as to obtain a time series of amperometric current measurements.

Figure 4B:
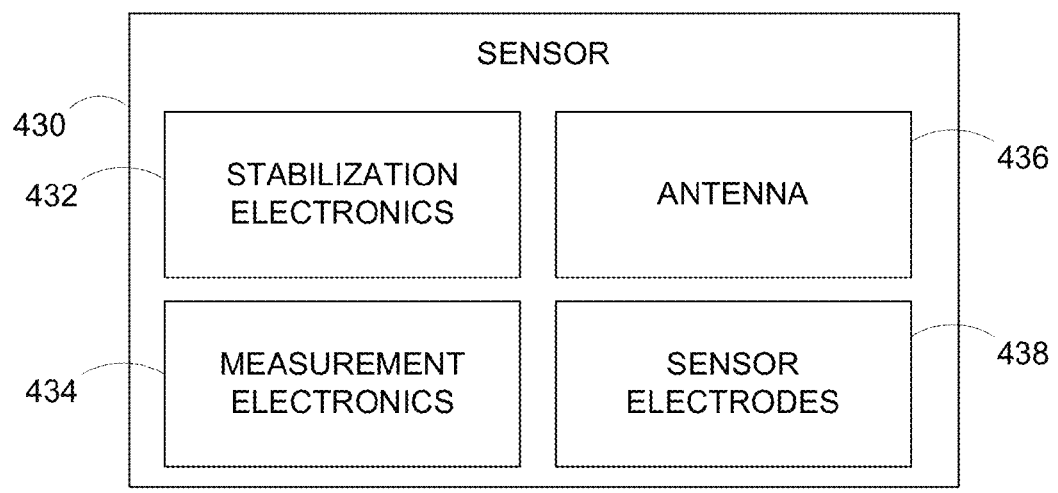
FIG. 4B is a block diagram of the ophthalmic electrochemical sensor system described in connection with FIG. 4A, in accordance with an example embodiment.

FIG. 4B is a block diagram of the ophthalmic electrochemical sensor 430 described in connection with FIG. 4A. The ophthalmic electrochemical sensor 430 can include stabilization electronics 432, measurement electronics 434, an antenna 436, and sensor electrodes 438. The stabilization electronics 432 can be configured to apply a stabilization voltage between the sensor electrodes 438 while the ophthalmic electrochemical sensor 430 is operating in a standby (or stabilization) mode. The measurement electronics 434 are configured to measure the amperometric current through the working electrode of the sensor electrodes 438 and communicate the measured amperometric current through the antenna 436.

Ophthalmic electrochemical sensor 430 can include energy harvesting systems for harvesting energy from incident radiation (and/or other sources) to generate bias voltage to apply across sensor electrodes during the standby mode. Ophthalmic electrochemical sensor 430 can also be configured to generate power from incident radiation to power measurement and communication electronics in response to receiving a measurement signal indicating initiation of an active measurement mode. For example, measurement electronics 434 can be configured to harvest energy from incident radio frequency radiation via the antenna 436 and use the harvested energy to power the measurement and communication of the amperometric current.

V. Example Eye-Proximate Readers

Figure 5:
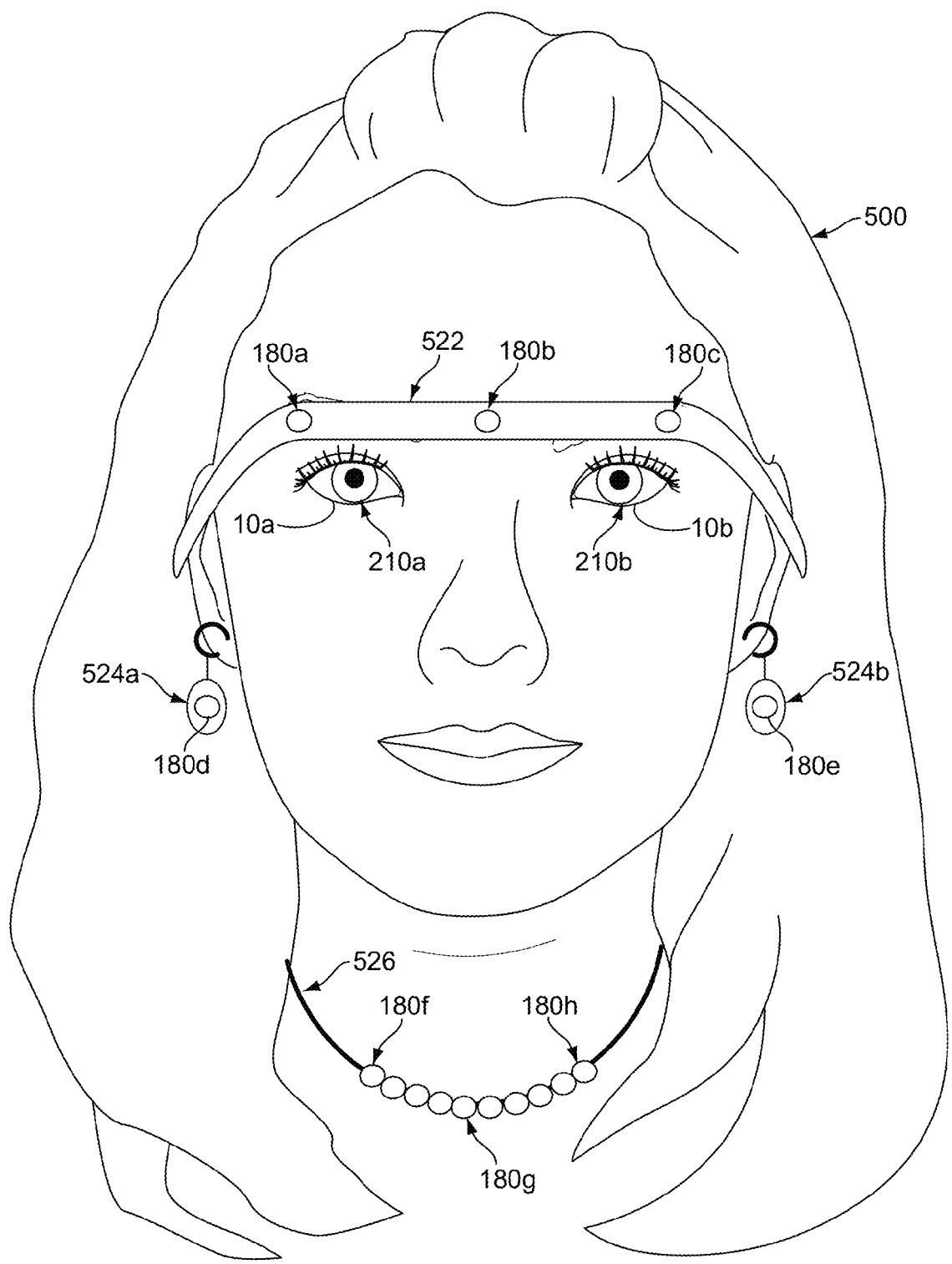
FIG. 5 shows an example wearer wearing two eye-mountable devices, a band, earrings, and a necklace, in accordance with an example embodiment.

FIG. 5 shows an example wearer 500 wearing two eye-mountable devices 210a, 210b, a band 522, earrings 524a, 524b, and a necklace 526. As discussed above at least in the context of FIGS. 3, 4A, and 4B, each eye-mountable device 210a, 210b can be configured with sensor(s) to measure at least current in the tear-film of an eye that the respective lens is worn in.

The functionality of band 522 can be performed by a structure of another device, e.g., an eye-glass frame, a head-mountable computer frame, a cap, a hat, part of a hat or cap (e.g., a hat band or bill of a baseball cap), a headphone headband, etc., or by a separate band; e.g., a head band, a scarf or bandanna worn as a head band. For examples, band 522 can be supported by ear(s), nose, hair, skin, and/or a head of wearer 500, and perhaps by external devices e.g., stick pins, bobby pins, headband elastics, snaps. Other and different support(s) for band 522 are possible as well.

One or more of band 522, earrings 524a, 524b, and necklace 526 can be configured to include one or more readers; e.g., the above-mentioned reader 180. FIG. 5 shows three example positions 180a, 180b, and 180c for readers in band 522. For example, if only eye-mountable device 210a has a sensor, then a reader, such as reader 180, can be mounted in example positions 180a and/or 180b to send commands and power to eye-mountable device 210a. Similarly, to power and communicate with a sensor in eye-mountable device 210b, a reader mounted in band 522, such as reader 180, can be mounted in example positions 180b and/or 180c.

Each of or both earrings 524a, 524b can be configured with respective readers 180d, 180e for communicating with and power sensors in respective eye-mountable devices 210a, 210b. Necklace 526 can be configured with one or more readers 180f, 180g, 180h for communicating with and power sensors in respective eye-mountable device 210a, 210b. Other embodiments are possible as well; e.g., readers in positions 180a-180c or near those positions can be configured as part of a hat, headband, scarf, jewelry (e.g., a brooch), glasses, HMD, and/or other apparatus.

In some embodiments, a reader can power a sensor in eye-mountable device 210 using a low-power transmission; e.g., a transmission of 1 watt or less of power. In these embodiments, the reader can be within a predetermined distance; e.g., 1 foot, 40 cm, of eye-mountable device 210a, 210b to power the sensor.

Figure 6:
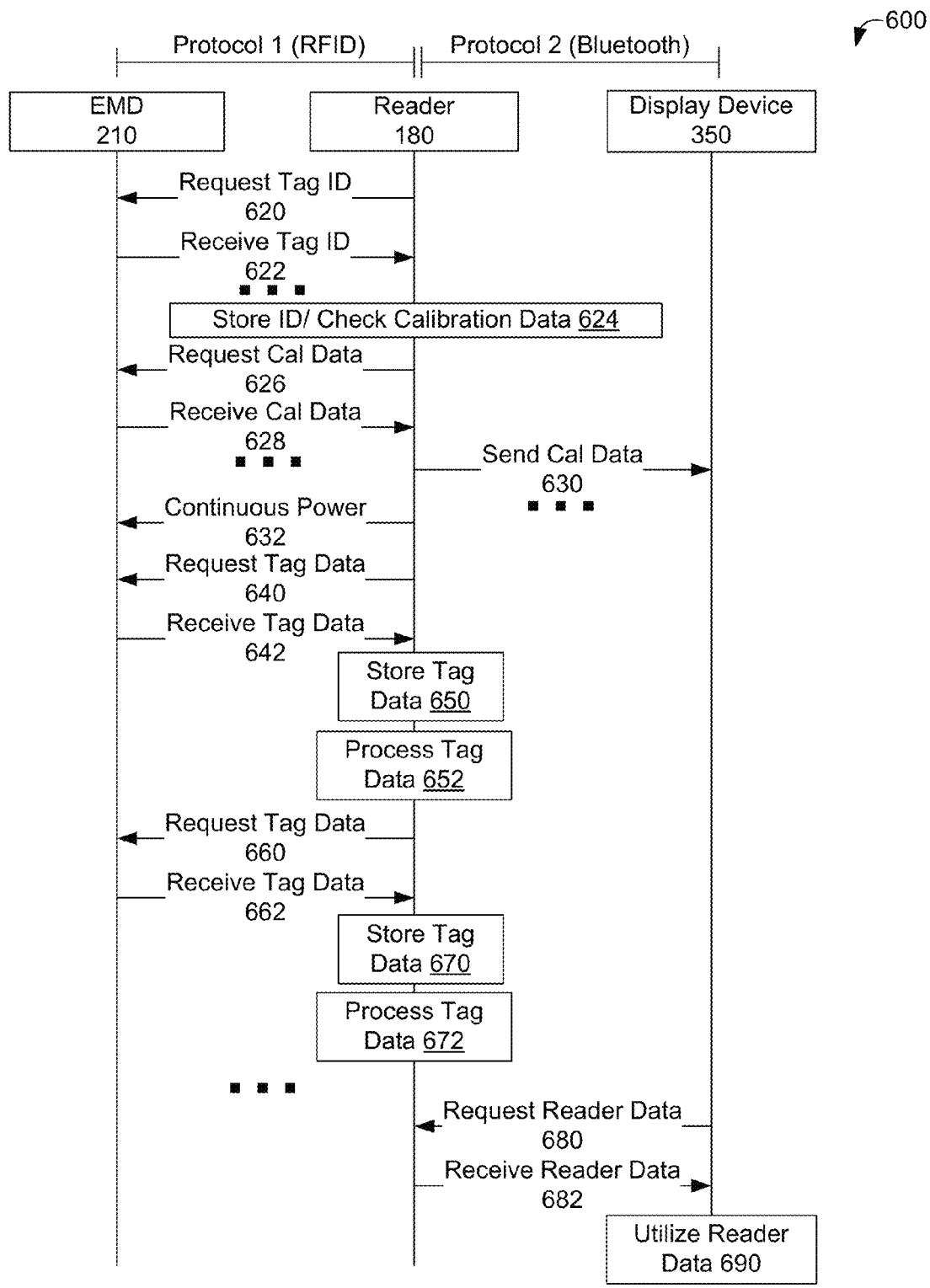
FIG. 6 shows a scenario where a reader communicates with an eye-mountable device and a display device, in accordance with an example embodiment.

FIG. 6 shows a scenario 600 where reader 180 communicates with eye-mountable device (EMD) 210 and display device 350. In scenario 600, eye-mountable device 210 and reader 180 communicate using an RFID protocol; e.g., an RFID Generation 2 protocol such as specified in "EPC™ Radio-Frequency Identity Protocols Class-1 Generation-2 UHF RFID Protocol for Communications at 860 MHz-960 MHz, Version 1.2.0", Oct. 23, 2008, EPCglobal Inc. In scenario 600, reader 180 and display device 350 communicate via a Bluetooth protocol; e.g., a protocol such as specified in "Specification of the Bluetooth System", Volumes 0-6, Core Package Version 4.0, Jun. 30, 2010, Bluetooth SIG, Inc.

In other scenarios, the reader, tag, display device, and/or other device(s) can communicate using different and/or additional protocols; e.g., an IEEE 802.11 protocol ("Wi-Fi"), an IEEE 802.15 protocol ("Zigbee"), a Local Area Network (LAN) protocol, a Wireless Wide Area Network (WWAN) protocol such as but not limited to a 2G protocol (e.g., CDMA, TDMA, GSM), a 3G protocol (e.g., CDMA-2000, UMTS), a 4G protocol (e.g., LTE, WiMAX), a wired protocol (e.g., USB, a wired IEEE 802 protocol, RS-232, DTMF, dial pulse). Many other examples of protocol(s) and combination(s) of protocols can be used as well.

Scenario 600 begins with reader 180 sending request tag ID message 620 to eye-mountable device 210. In response to request tag ID message 620, eye-mountable device 210 can retrieve its identifier (ID) and send the ID in receive tag ID message 222 to reader 180. In environments where multiple eye-mountable devices and/or other device(s) with tags are operating, reader 180 can send a number of tag ID messages 620 to the devices with operating tags to obtain IDs for all of the multiple devices with operating tags and responsively receive a number of receive tag ID messages 622. In some embodiments, one tag ID message 620 can lead to multiple receive tag ID messages 622 being sent; e.g., one receive tag ID message from each of multiple devices with operating tags. In scenario 600, only one device—eye mountable device 210—has an operating tag and, thus, only one receive tag ID message 622 is received by reader 180 in response to request tag ID message 620.

Upon receiving the ID(s) (or other identifying information) for eye-mountable device 210, reader 180 can determine store the ID 624 and determine whether calibration data is available for the eye-mountable device. Some types of calibration data can be determined on a per-device basis; e.g., in scenario 600, calibration data for converting current data received from an analyte bio-sensor to concentration of the analyte in tear-film can be determined on a per-device basis. For example, an analyte bio-sensor configured to measure glucose can have calibration data to convert current data to tear-film glucose levels. The calibration data can be determined at time of manufacture of the bio-sensor; e.g., by taking current measurements using the bio-sensor (or equivalent device) in samples of liquids (e.g., water or artificial tear film) having different amounts of glucose dissolved in each liquid sample. Then, based on the measured current values, one or more mathematical models for converting current values to tear-film glucose levels can be determined. Example mathematical models include, but are not limited to, a linear model, a piecewise linear model, a quadratic model, a cubic model, a logarithmic model, an exponential model, or another type of non-linear model. The mathematical model can take the calibration data and current data as inputs and determine a tear-film glucose model as output.

Other types of calibration data can be determined on a per-person or per-wearer basis; e.g., in scenario 600, calibration data for converting tear-film glucose data to blood-glucose data can be determined on a per-wearer basis. This calibration data can be determined only after a wearer (or person) has worn the bio-sensor and the calibration data determined. For example, to calibrate reader 180, a wearer of eye-mountable sensor 210 can press a calibration button of reader 180 shortly after finishing a meal so that reader 180 can determine relatively high and relatively low blood-glucose levels for the wearer, and use those values as calibration data inputs to a mathematical model for converting current values and/or tear-film glucose levels to blood-glucose levels. The mathematical model can be one or more of the example mathematical models listed above; e.g., a linear model, a piecewise linear model, etc. Other types of per-device and/or per-wearer calibration data are possible as well.

In scenario 600, reader 180 does not have calibration data for eye-mountable device 210 based on the ID provided in receive tag ID message 622. In response, reader 180 can generate one or more request calibration data messages 626 and receive, in response, one or more receive calibration data messages 628. The request calibration data messages 626 can include requests for one or more different types of calibration data; e.g., current to tear-film glucose calibration data, tear-film glucose to blood-glucose calibration data, data values for reader 180 to calculate calibration data. In scenario 600, reader 180 provides some or all of the calibration data to display device 350 via send calibration data message(s) 630 to permit display device 350 to perform some or all of the processing related to sensor data from eye-mountable device 210. For example, reader 180 can use calibration data message(s) 630 to send calibration data to convert tear-film glucose data received by reader 180 from an identified eye-mountable device to blood-glucose values, which display device 350 can then display to the wearer of the identified eye-mountable device. In other scenarios, display device 350 can send one or more request calibration data messages to reader 180 to request calibration data.

RFID tags, such as tag 370 of eye-mountable device 210, can be passive tags. A passive RFID tag can be configured to receive radio-frequency (RF) signals and to store power provided in the RF signals. The RF signals may or may not include RFID messages. For example, reader 180 can continuously send request tag ID messages to tag(s) within range of reader 180 in order to provide power to the in-range tag(s); e.g., tag 370. In some embodiments, reader 180 can send radio-frequency (RF) signals that are not RFID messages; e.g., a continuous RF waveform, to provide periodic or continuous power to a tag. FIG. 6 shows an example of providing continuous power 632 from reader 180 to eye-mountable device 210.

Scenario 600 can continue with reader 180 sending request tag data message 640 to eye-mountable device 210 to obtain data from eye-mountable device 210; e.g., data from one or more sensor(s) mounted on the contact lens and configured to communicate sensor data to the tag. Eye-mountable device 210 can provide the requested data in receive tag data message 642. Upon reception of the data from eye-mountable device 210, reader 180 can store the tag data 650 and/or process the tag data 652, such as discussed in the glucose example above. Reader 180 can periodically request data from eye-mountable device 210, such as by sending one or more request tag data messages 660 to eye-mountable device 210 and responsively receiving receive tag data message 662. In some embodiments, reader 180 can determine if the contact lens has enough power to operate the sensor and send tag data in response to a request. For example, reader 180 can determine the power available to eye-mountable device 210 based on a determination of power provided by reader 180 to eye-mountable device 210, by measuring a signal strength of message(s) received from eye-mountable device 210, by power-related data included in message(s) received from eye-mountable device 210, and/or by other techniques. Upon receiving tag data in receive tag data message 662, reader 180 can store the tag data 670 and/or process the tag data 672.

At some time, display device 350 can send request reader data message 680 to reader 180 to request data from reader 180 and/or eye-mountable device 210. In some scenarios not shown in FIG. 6, upon reception of request reader data message 680, reader 180 can send a request tag data message to obtain data from eye-mountable device 210 and subsequently store and/or process the data requested from eye-mountable device 210. After receiving request reader data message 680, reader 180 can generate and send receive reader data message 682 that includes data stored and/or processed by reader 180 to display device 350. In some embodiments, multiple messages may be used to perform the functionality of receive reader data message 682 and/or any other message described in scenario 600. In some embodiments not shown in FIG. 6, reader 180 can initiate data transmission to display device 350 when reader data is available, periodically, or using some other criteria; i.e., reader 180 can push reader data to the display device.

After receiving data from reader 180 in receive reader data message 682, display device 350 can utilize reader data 690; e.g., process, present, store, communicate, and/or otherwise use reader data 690. For example, if reader data 690 includes tear-film glucose data, then display device 350 can process the tear-film glucose data to generate blood-glucose data. Upon generation of blood-glucose data, display device 350 can present the blood-glucose data using visual and/or audio means (e.g., using display(s), speaker(s), bone conduction transducer(s), etc.).

In some embodiments, display device 350 can evaluate the blood-glucose data. For example, display device 350 can compare blood-glucose data to low-glucose and/or high-glucose threshold(s) to determine, respectively, whether the blood-glucose data is too high or low for wearer 100 of eye-mountable device 210. If the blood-glucose data is too high or low for wearer 100, display device 350 can alert wearer 100, attempt to contact another person or entity associated with wearer 100 to help wearer 100, and/or perform some other action. As another example, display device 350 can have an interface with an insulin pump or similar device configured to provide insulin to wearer 100. Then, if the blood-glucose data is too high, display device 100 can, via the interface, instruct the insulin pump to provide insulin to wearer 100. Other examples are possible as well.

VI. Example Display Device Views

FIGS. 7A-7E show example views 710, 720, 730, 740, and 750 of a user interface for a display device 350. Views 710, 720, 730, 740, and/or 750 can be presented by one or more applications executing on display device 350; e.g., a blood glucose meter and graph application. The display device can be configured to display blood glucose levels, which can be or correspond to the blood-glucose data and/or blood glucose concentration values discussed above.

FIG. 7A shows example glucose meter view 710 indicating a "Normal" blood glucose level of "5.0" measured using "mmol/L" values (millimoles per liter of blood). FIG. 7A shows view 710 with a background color of white to indicate a normal blood glucose level; other colors and/or patterns (e.g., green background for a traffic-light color scheme, a large watermarked "OK", a thumbs-up image) can be used instead of a white background to designate a normal blood glucose level. View 710 indicates that a time of "9:18 PM" when the blood glucose level was measured and a current time of "9:20". In some embodiments, audio data representing part or all of the content of views 710, 720, 730, 740, and/or 750 can be provided with or instead of the corresponding views; e.g., text such as "Your Blood Glucose Level is 5.0 which is Normal" can be converted to speech and presented using a speaker or similar audio-output device of display device 350.

View 710 also includes three buttons 712a, 714, and 716a. Button 712a marked "Graph" can be configured to, when selected, instruct display device 350 to draw a glucose graph, or graph of blood glucose levels over time. Button 714 marked "Settings" can be configured to, when selected, instruct display device 350 to display and/or enable changing of various settings related to the glucose meter and glucose graph. Button 716a marked "mg/DL" can be configured to, when selected, instruct display device 350 to display blood glucose levels using milligrams of glucose per deciliter of blood (mg/DL) values. In some embodiments, the blood glucose meter and graph application can be terminated by selection of a button not shown in the Figures; e.g., a back or exit button.

FIG. 7B shows example glucose meter view 720 indicating an "Elevated" blood glucose level of "160.1" measured using "mg/DL" values. FIG. 7B shows view 720 with a background color of grey to indicate an elevated blood glucose level; other colors and/or patterns (e.g., yellow background for a traffic-light color scheme, a large watermarked "Warning", an image of a warning sign) can be used instead of a grey background to designate an elevated blood glucose level. View 720 indicates that a time of "9:18 PM" when the blood glucose level was measured and a current time of "9:20". View 720 also includes button 716b marked "mmol/L". Button 716b can be configured to, when selected, instruct display device 350 to display blood glucose levels using millimole per liter (mmol/L) values.

FIG. 7C shows example glucose meter view 730 indicating an "Elevated" blood glucose level of "11.9" measured using "mmol/L" values. FIG. 7C shows view 720 with a background color of black to indicate an elevated blood glucose level; other colors and/or patterns (e.g., red background for a traffic-light color scheme, a large watermarked "Danger", an image of a siren or other emergency equipment) can be used instead of a black background to designate a high blood glucose level. View 720 indicates that a time of "9:18 PM" when the blood glucose level was measured and a current time of "9:20".

View 730 also includes buttons 732a, 732b each marked "Call Help". Buttons 732a and 732b can each be configured to, when selected and when authorized by a person associated with display device 350, instruct display device 350 to originate a telephone call or other type of message to a help number; e.g., an emergency services number (e.g., 911), spouse, other relative, friend, health service. For example, when button 732a is selected, a text message can be sent and/or a telephone call can be originated to the help number. In some embodiments, the telephone call can include at least an automated portion of the call. In still other embodiments, the help number can include an e-mail address, and the call for help can include an e-mail to the e-mail address included with the help number.

An example text/e-mail message or text for an automated (portion of a) telephone call can be "<P1> has a high blood glucose reading of <X><Y> and has asked you for help. Please assist!", where <P1> can be replaced with a name of a person associated with display device 350; e.g., the owner of display device 350, <X> can be replaced with the blood glucose reading value; e.g., 11.9 in view 730, and <Y> can be replaced with the unit measure used for the blood glucose reading value; e.g., mmol/L in view 730. In some embodiments, <P1> can be replaced or augmented by text related to a telephone directory number or other identifier (e.g., device name, user name, Internet Protocol address) related to display device 350; e.g., <P1> can be "<name>, who is associated with phone number <phoneno>," or can be "The person associated with <phoneno>", where <name> is the name of the person associated with display device 350 and <phoneno> is the directory number associated with display device 350.

In some embodiments, a call for help can be made automatically if both authorized by the person associated with display device 350 and the blood glucose level remains above a predetermined value for at least a predetermined amount of time. In other embodiments, views 710, 720, and 730 can be used to display historical blood glucose levels; e.g., the blood glucose meter and graph application can display stored past blood glucose levels for a given previous time or range of times.

Figure 7D:
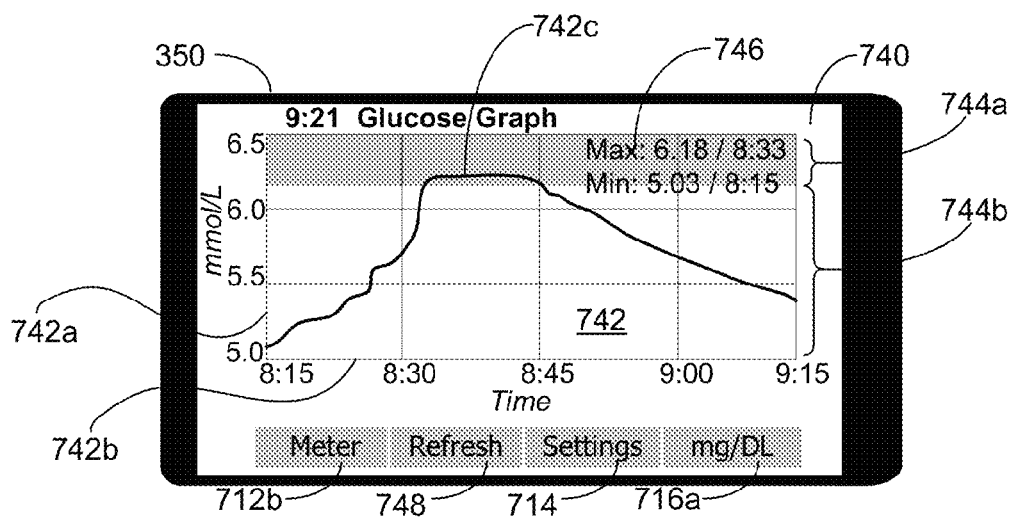

FIG. 7D shows an example view with graph 740 of blood glucose levels over one hour's time. Graph 740 has vertical axis 742a for blood glucose levels and horizontal axis 742b for time. In the example shown in FIG. 7D, vertical axis 742a shows blood glucose levels measured in measured in mmol/L and with a possible range from 5.0 to 6.5, and horizontal axis 742b shows time starting at 8:15 and ending at 9:15. FIG. 7D also shows display device 350 with a current time of 9:21.

Graph 740 includes a portion 744a showing elevated blood glucose levels, depicted as a grey band, and portion 744b showing normal blood glucose levels, depicted as a white band. Data region 746 of graph 740 shows a maximum blood glucose level of "6.18" at a time of "8:33" and minimum blood glucose level of "5.03" at a time of "8:15".

In some embodiments not shown in FIG. 7D, a current and/or average blood glucose level can be displayed a part of data region 746 or in another portion of graph 740. In other embodiments not shown in FIG. 7D, a graphical display; e.g., a thermometer-style display, can be used to show minimum, maximum, current, average, and/or other specific blood glucose levels.

FIG. 7D shows the view with button 712b marked "Meter", which can be configured to, when selected, instruct display device 350 to display a glucose meter; e.g., display one of views 710, 720, or 730. FIG. 7D shows the view with button 748 marked "Refresh". Button 748 can be configured to, when selected, instruct display device 350 to refresh graph 740, or re-display graph 740 using data most recently received; e.g., from reader 180.

Figure 7E:
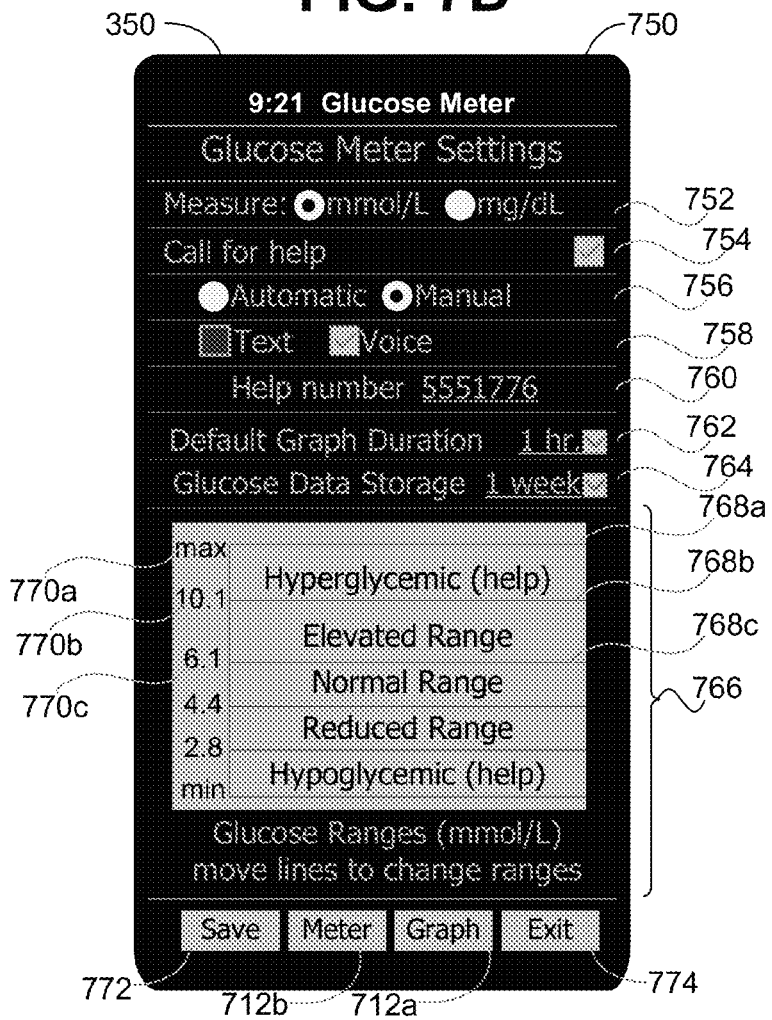

FIG. 7E shows a "Glucose Meter Settings" view 750 for reviewing and/or changing values related to the blood glucose meter and graph application. FIG. 7E shows view 750 with measurement setting 752, call for help settings 752, 754, 756, 758, and 760, graph settings 762-770c, and buttons 712a, 712b, 772, and 774. Measurement setting 752 can be used to select units of measurement for the blood glucose meter and graph application; e.g., mmol/L or mg/dL.

Call for help setting 754 is configured to enable or disable the call for help feature of the blood glucose meter and graph application discussed above in the context of at least FIG. 7C. FIG. 7E shows call for help setting 754 with a check mark to indicate that the call for help feature is currently enabled. Automatic/manual setting 756 can be used to select whether calls for help are made automatically by display device 350 e.g., upon detection of one or more conditions discussed above in the context of FIG. 7C and without any intervention by a person; or manually e.g., the call is made upon selection of a button, such as button 732a or 732b. Text/voice setting can be used to select whether calls for help are made using a text-based service e.g., text message or e-mail, and/or a voice-based service. In the example shown in FIG. 7C, calls for help will be made using only a voice-based service, as the "Text" setting is shown as not checked and the "Voice" setting is shown as checked. Help number 760 can be used to specify a number to use for placing calls for help. In some embodiments not shown in FIG. 7E, help e-mail address(es) and/or multiple help numbers can be specified.

Graph duration setting 762 can be used to configure a duration for a blood glucose graph. In the example shown in FIG. 7E, one hour is used; while in other examples, shorter durations such as, but not limited to, 15 or 30 minutes, can be selected, and in even other examples, longer durations, such as, but not limited to, multiple hours, a day, or multiple days can be selected. Glucose data storage setting 764 can be used to allocate an amount of storage used to store blood glucose data for review and display. For example, if the data to store blood glucose levels for one day is X megabytes, then selecting a glucose data storage of "1 week" as shown in FIG. 7A can cause display device 350 to allocate at least 7× megabytes for storing blood glucose levels.

Glucose range setting 766 can be used to select blood glucose values corresponding to a number of glucose level ranges. FIG. 7E shows five example glucose level ranges: a high or hyperglycemic range, an elevated range, a normal range, a reduced range, and a low or hypoglycemic range. For example, FIG. 7E shows the elevated range bounded by lines 768b and 768c, with line 768b separating the hyperglycemic and elevated ranges associated with blood glucose level 770b of "10.1" mmol/L, and line 768c separating the elevated and normal ranges associated with blood glucose level 770c of "6.1" mmol/L. Mmol/L values are used by glucose range setting 766 in accord with measurement setting 752. Thus, in this example, blood glucose levels between 6.1 and 10.1 mmol/L fall into the elevated range. As other examples, values between 10.1 mmol/L and a maximum blood glucose level 770a; that is, values above 10.1 mmol/L, are in the hyperglycemic range, while values below 2.8 mmol/L are in the hypoglycemic range.

To change blood glucose level(s) associated with glucose range(s), a user of view 750 can use a touch screen or other input device to select a line separating glucose ranges and then move the line up or down within glucose range setting 766. For example, if display device 350 is configured with a touch screen, a user can select line 770b by touching a portion of the screen display displaying line 770b with a finger, stylus, or other selection indicator, and moving the selection indicator up or down to adjust the range. In this example, a user can touch line 770b with a figure and move his or her finger up to change an upper bound of the elevated range from 10.1 to a higher value; e.g., 11.0 mmol/L or move his or her finger down to change the upper bound of the elevated range to a lower value; e.g., 9.5 mmol/L.

Button 772 marked "Save" can be configured to, when selected, instruct display device 350 to save settings as indicated in glucose meter settings view 750. Button 775 marked "Exit" can be configured to, when selected, instruct display device 350 to exit the glucose meter settings view 750 and/or the blood glucose meter and graph application without saving changed setting values.

VII. Example Operations

Figure 8:
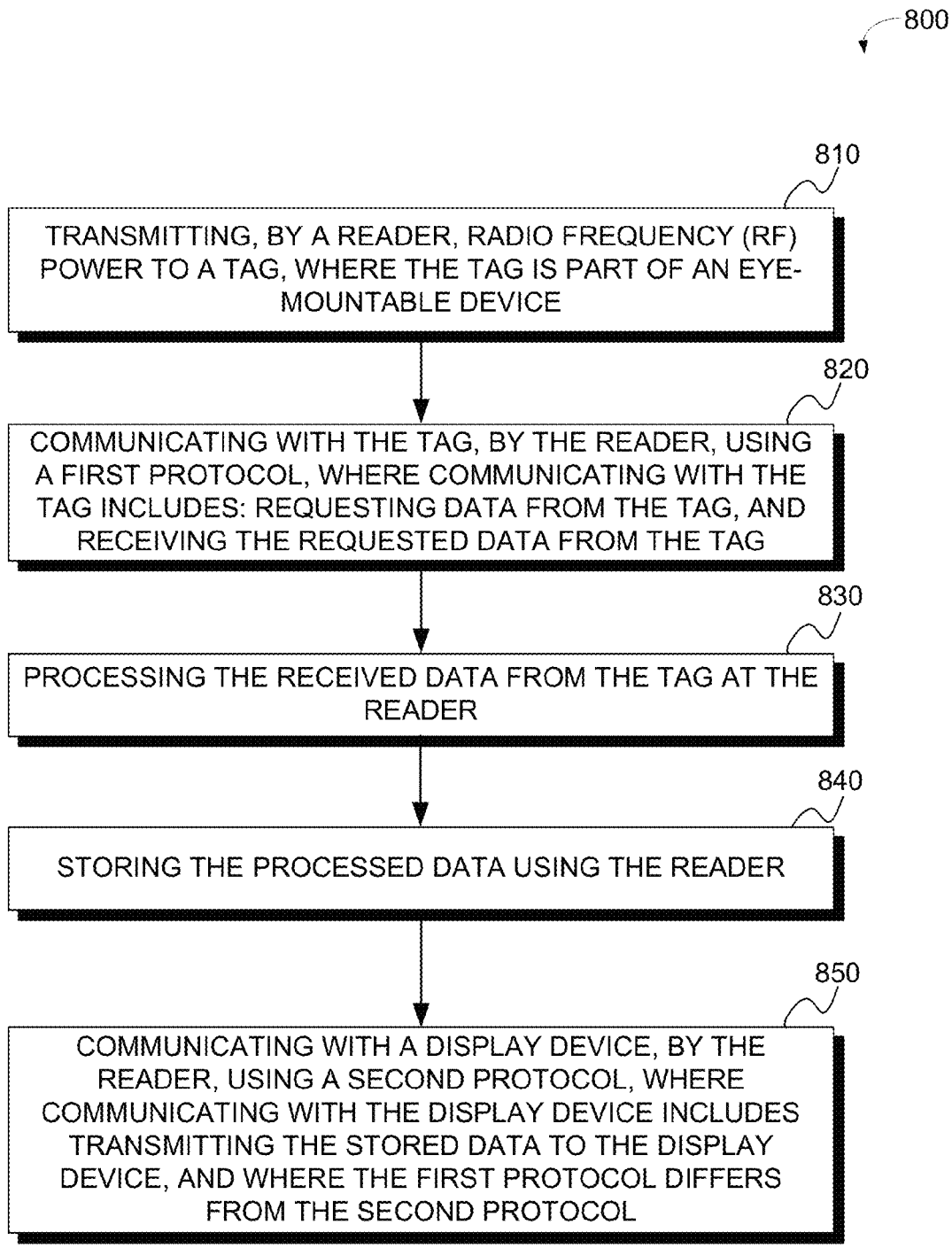
FIG. 8 is a flow chart of an example method, in accordance with an example embodiment.

FIG. 8 is a flow chart of an example method 800. Method 800 can be carried out by a reader, such as reader 180, or a device that includes a processor, such part of processing system 346, with a computer readable medium storing machine-readable instructions, where the machine-readable instructions, when executed by the processor of the device, are configured to cause the device to carry out some or all of the techniques described herein as method 800.

Method 800 can begin at block 810. At block 810, the reader can transmit RF power to a tag, such as discussed above in the context of at least FIG. 6. The tag can be part of an eye-mountable device; e.g., tag 370 of eye-mountable device 210, such as discussed above in more detail in the context of at least FIG. 3. In some embodiments, the reader can be within a predetermined distance from the tag when transmitting RF power to the tag, such as discussed above in the context of at least FIG. 5. In other embodiments, the reader can be part of an HMD, such as discussed above in the context of at least FIG. 5.

At block 820, the reader can communicate with the tag using a first protocol. Communicating with the tag can include requesting data from the tag and receiving the requested data from the tag, such as discussed above in the context of at least FIG. 6. In some embodiments, communicating with the tag can also include: sending a request for an identifier (ID) of the tag using the first protocol and, in response to the request for the ID of the tag, receiving a message that includes the ID of the tag, such as discussed above at least in the context of FIG. 6.

In other embodiments, requesting data from the tag can include requesting one or more sensor measurements from the tag, such as discussed above at least in the context of FIG. 6. In still other embodiments, the reader can transmit the RF power to the tag for at least a predetermined period of time before requesting the one or more sensor measurements, such as discussed above at least in the context of FIG. 6.

At block 830, the reader can process the data received from the tag, such as discussed above in the context of at least FIG. 6. In some embodiments, processing the received data can include determining a tear-film glucose concentration based on the one or more sensor measurements, such as discussed above in the context of at least FIG. 6. In particular embodiments, a blood glucose concentration can be determined based on the tear-film glucose concentration, such as discussed above in the context of at least FIGS. 1 and 6. In other particular embodiments, the display device can display the blood glucose concentration, such as discussed above in the context of at least FIGS. 6 and 7.

At block 840, the reader can store the processed data, such as discussed above in the context of at least FIG. 6.

At block 850, the reader can communicate with a display device using a second protocol, such as discussed above in the context of at least FIG. 6. Communicating with the display device can include transmitting the stored data to the display device. The first protocol can differ from the second protocol.

In some embodiments, communicating with the display device can include receiving a request for the stored data from the display device, such as discussed above in the context of at least FIG. 6. In other embodiments, the first protocol can be a Radio-Frequency Identification (RFID) protocol, and the second protocol can be a Bluetooth protocol, such as discussed above in the context of at least FIGS. 3 and 6.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A method, comprising:
transmitting, by a reader, radio frequency (RF) power to a sensing device, wherein the sensing device is physically separated from the reader, and wherein the sensing device includes a sensor configured to obtain measurements related to glucose in a bodily fluid;
communicating with the sensing device, by the reader, using a first wireless protocol, wherein communicating with the sensing device comprises requesting and receiving one or more measurements by the sensor;
determining first calibration data based on an identifier of the sensing device;
determining a glucose concentration in the bodily fluid based on the one or more measurements and the first calibration data, wherein determining the glucose concentration in the bodily fluid based on the one or more measurements and the first calibration data comprises determining the glucose concentration in the bodily fluid by a processing system in the reader, wherein the processing system comprises one or more processors and one or more storage components;
receiving user input from a user of the sensing device;
responsive to receiving the user input, determining second calibration data specific to the user, wherein determining second calibration data specific to the user comprises determining two different blood glucose levels for the user;
determining a blood glucose concentration based on the glucose concentration in the bodily fluid and the second calibration data; and
providing, by a user interface, an indication of the blood glucose concentration.

2. The method of claim 1, further comprising:
instructing, by the processing system, the user interface to provide the indication of the blood glucose concentration.

3. The method of claim 2, wherein the indication of the blood glucose concentration comprises at least one of a visual indication from the reader or an audio indication from the reader.

4. The method of claim 1, wherein the user interface is in a display device external to the reader.

5. The method of claim 4, wherein the indication of the blood glucose concentration comprises at least one of a textual indication or a graphical indication on a display of the display device.

6. The method of claim 4, wherein the display device is a wearable computer, handheld computer, tablet computer, or mobile phone.

7. The method of claim 4, further comprising:
transmitting data from the reader to the display device using a second wireless protocol, wherein the data relates to the glucose concentration in the bodily fluid.

8. The method of claim 7, wherein the second wireless protocol is a Bluetooth protocol.

9. The method of claim 8, wherein the first wireless protocol is a Radio-Frequency Identification (RFID) protocol.

10. A non-transitory computer-readable storage medium having stored thereon program instructions that, upon execution by a processor of a computing device, cause the computing device to perform functions comprising:
transmitting radio frequency (RF) power to a sensing device, wherein the sensing device is physically separated from the computing device, and wherein the sensing device includes a sensor configured to obtain measurements related to glucose in a bodily fluid;
communicating with the sensing device using a first wireless protocol, wherein communicating with the sensing device comprises requesting and receiving one or more measurements by the sensor;
determining first calibration data based on an identifier of the sensing device;
determining a glucose concentration in the bodily fluid based on the one or more measurements and the first calibration data;
receiving user input from a user of the sensing device;
responsive to receiving the user input, determining second calibration data specific to the user, wherein determining second calibration data specific to the user comprises determining two different blood glucose levels for the user;
determining a blood glucose concentration based on the glucose concentration in the bodily fluid and the second calibration data; and
instructing a user interface to provide an indication of the blood glucose concentration.

11. The non-transitory computer-readable storage medium of claim 10, wherein the indication of the blood glucose concentration comprises at least one of a visual indication from the computing device or an audio indication from the computing device.

12. The non-transitory computer-readable storage medium of claim 10, wherein the user interface is in a display device external to the computing device.

13. The non-transitory computer-readable storage medium of claim 12, wherein the functions further comprise:
transmitting data to the display device using a second wireless protocol.

14. The non-transitory computer-readable storage medium of claim 13, wherein the first wireless protocol is a Radio-Frequency Identification (RFID) protocol and the second wireless protocol is a Bluetooth protocol.

15. A computing device, comprising:
an antenna;
a processor; and
a non-transitory computer readable medium storing instructions thereon that, when executed by the processor, cause the computing device to perform functions comprising:
transmitting radio frequency (RF) power to a sensing device using the antenna, wherein the sensing device is physically separated from the computing device, and wherein the sensing device includes a sensor configured to obtain measurements related to glucose in a bodily fluid;
communicating with the sensing device using a first wireless protocol, wherein communicating with the sensing device comprises requesting and receiving one or more measurements by the sensor;
determining first calibration data based on an identifier of the sensing device;
determining a glucose concentration in the bodily fluid based on the one or more measurements and the first calibration data;
receiving user input from a user of the sensing device;
responsive to receiving the user input, determining second calibration data specific to the user, wherein determining second calibration data specific to the user comprises determining two different blood glucose levels for the user;

determining a blood glucose concentration based on the glucose concentration in the bodily fluid and the second calibration data; and instructing a user interface to provide an indication of the blood glucose concentration.

16. The computing device of claim 15, wherein the indication of the blood glucose concentration comprises at least one of a visual indication from the computing device or an audio indication from the computing device.

17. The computing device of claim 15, wherein the user interface is in a display device external to the computing device, and wherein the functions further comprise transmitting data to the display device using a second wireless protocol.

18. The method of claim 1, wherein the sensing device is an eye-mountable device, and wherein the bodily fluid is tear fluid.

19. The non-transitory computer-readable storage medium of claim 10, wherein the sensing device is an eye-mountable device, and wherein the bodily fluid is tear fluid.

20. The computing device of claim 15, wherein the sensing device is an eye-mountable device, and wherein the bodily fluid is tear fluid.

* * * * *